United States Patent [19]
Gray

[11] Patent Number: 6,024,762
[45] Date of Patent: Feb. 15, 2000

[54] THERAPEUTIC PILLOW

[76] Inventor: J. Todd Gray, P.O. Box 451, Amarillo, Tex. 79105

[21] Appl. No.: 09/062,769

[22] Filed: Apr. 20, 1998

[51] Int. Cl.[7] .................................. A61F 7/00; A47G 9/00
[52] U.S. Cl. .............................. 607/109; 607/104; 5/636
[58] Field of Search ..................... 607/108, 109, 607/112, 114; 5/636, 639, 644, 441; 62/530

[56] References Cited

U.S. PATENT DOCUMENTS

| | | |
|---|---|---|
| 926,563 | 6/1909 | Hobson . |
| 1,018,685 | 2/1912 | Smith . |
| 3,981,032 | 9/1976 | Brooks ......................................... 5/338 |
| 4,783,866 | 11/1988 | Simmons et al. ............................. 5/441 |
| 4,887,326 | 12/1989 | O'Brian et al. .............................. 5/421 |
| 5,163,194 | 11/1992 | Dixon .......................................... 5/636 |
| 5,344,437 | 9/1994 | Pistay ....................................... 607/109 |
| 5,457,832 | 10/1995 | Tatum . |
| 5,481,771 | 1/1996 | Burk, IV . |
| 5,577,995 | 11/1996 | Walker et al. . |
| 5,577,996 | 11/1996 | Gardner et al. . |
| 5,716,388 | 2/1998 | Petelle ..................................... 607/108 |
| 5,933,890 | 8/1999 | Codd ........................................... 5/636 |

*Primary Examiner*—Linda C. M. Dvorak
*Assistant Examiner*—Roy Gibson
*Attorney, Agent, or Firm*—Dowell & Dowell, P.C.

[57] ABSTRACT

A head supporting therapeutic pillow including an outer cover containing a pair of spaced pressure stimulators, a layer of cushioning material and a freezable liquid enclosed in at least one flexible pouch. The pressure stimulators are preferably spaced apart by a stabilizer bar. In a preferred method of use, the pillow is placed on the back of an individual's neck while the liquid is in a frozen or semi-frozen state. In an alternative embodiment, the pillow includes slots for supporting a strap enabling the pillow to be worn.

17 Claims, 2 Drawing Sheets

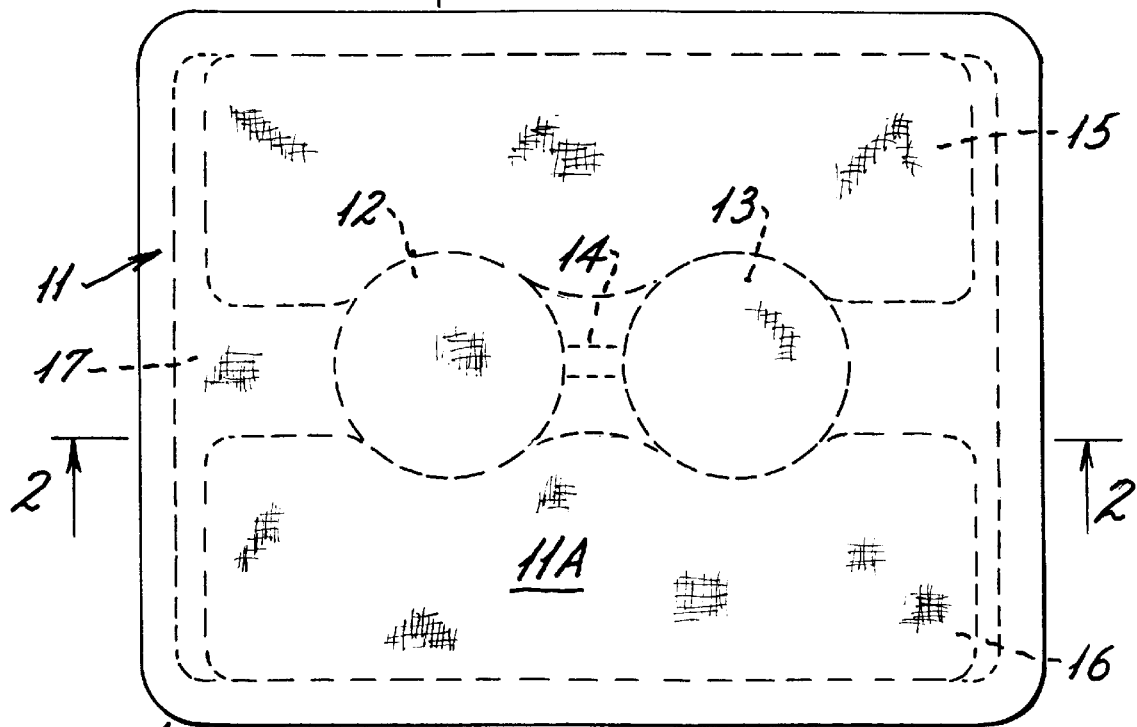
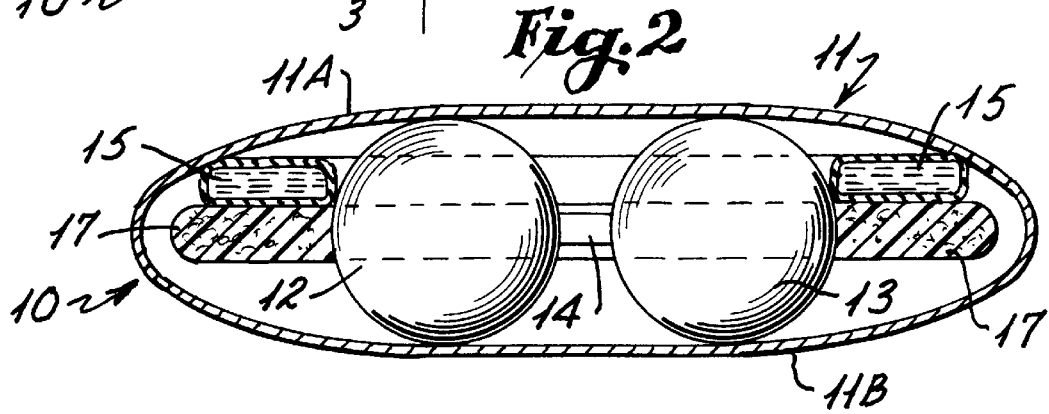
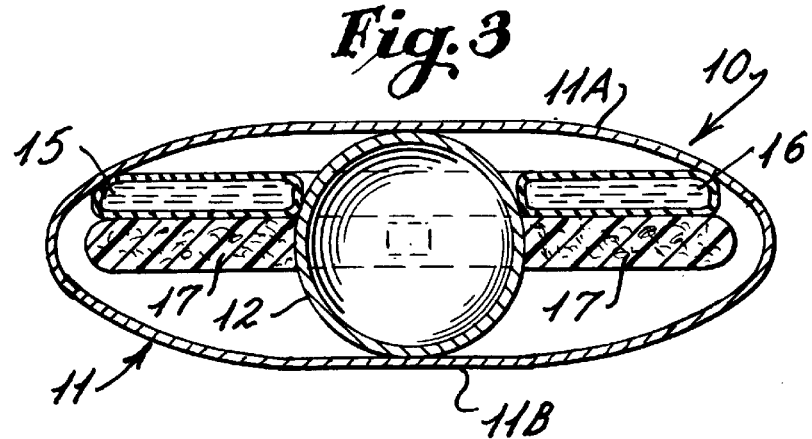

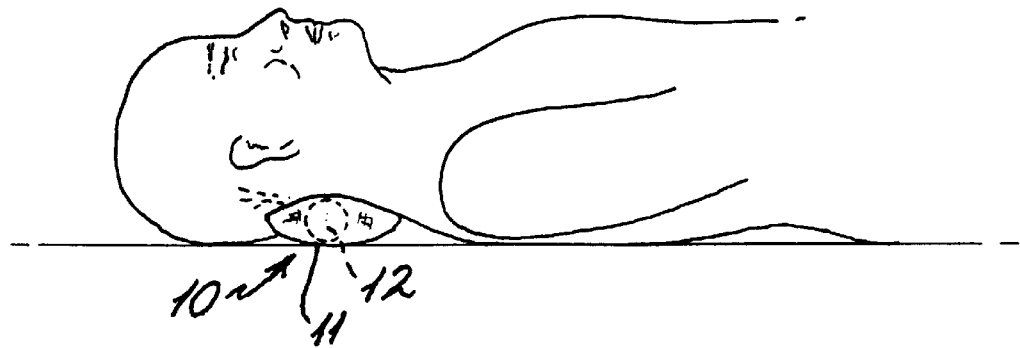
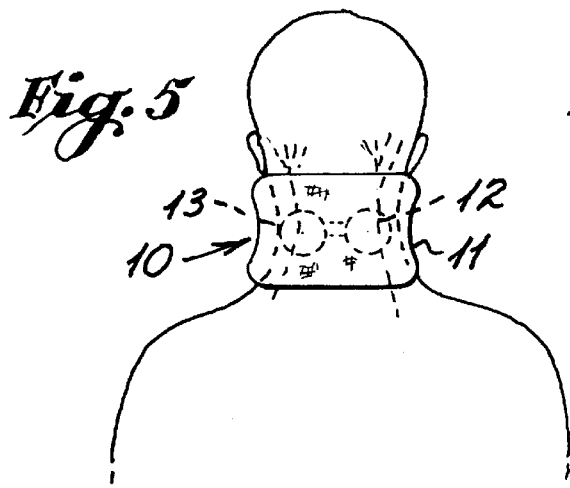
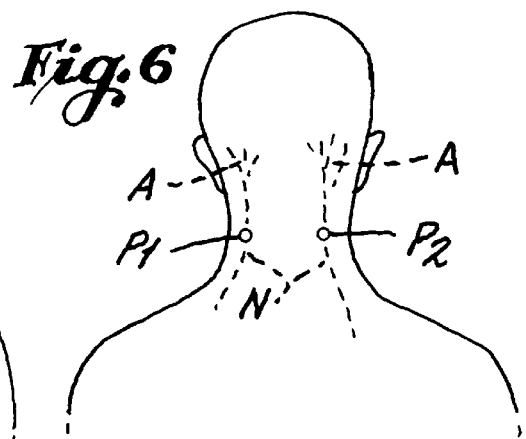
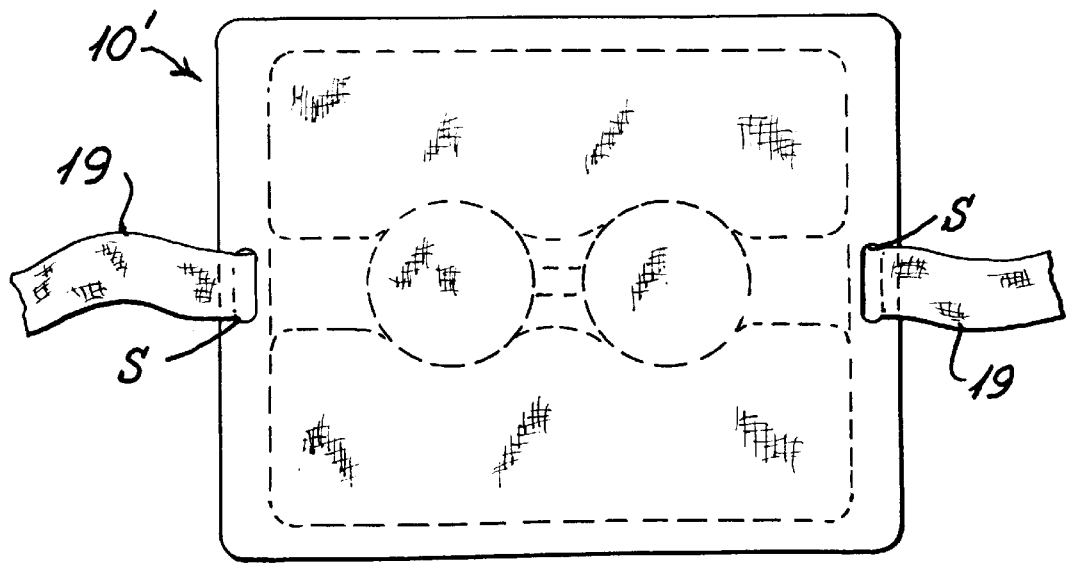

THERAPEUTIC PILLOW

CROSS REFERENCES TO RELATED APPLICATIONS

None

STATEMENT AS TO RIGHTS TO INVENTIONS MADE UNDER FEDERALLY SPONSORED RESEARCH AND DEVELOPMENT

None

BACKGROUND OF THE INVENTION

This invention is generally directed to head supporting pillows and, more particularly, to a therapeutic muscle tension relieving pillow for treating headaches.

Tension produced in cervical muscles has been linked to the onset of headaches. It has been estimated that ninety percent of all headaches are muscular-tension related. Pressure from tension increases pressure on the greater occipital nerve and the occipital arteries resulting in a reduced blood supply which has been shown to be a contributing factor in headache pain. In the past, efforts have been made to fabricate massage type devices to reduce or eliminate the causes of such headaches. For example, U.S. Pat. No. 5,481,771 discloses a pillow having a pair of hemispherically shaped projections in an upper surface. However, the device cannot be used to provide both pressure and temperature stimulation.

SUMMARY OF THE INVENTION

In accordance with the present invention, a head supporting therapeutic pillow includes an outer cover containing a pair of spaced spherical-shaped pressure stimulators, a layer of cushioning material and a freezable liquid enclosed in one or more flexible pouches. The pressure stimulators are preferably spaced apart by a stabilizer bar. In a preferred method of use, a user presses the back of their neck against the pillow while the liquid is in a frozen state. In an alternative embodiment, the pillow includes slots for supporting a strap enabling the pillow to be conveniently worn in a standing or other position. The therapeutic pillow may also be used for treatment of stress relief and pain along the lower back of the spinal column.

It is an object of the present invention to provide an improved therapeutic head supporting pillow of simple and compact construction which can provide a therapeutic effect against tension and migraine headaches and/or their onset without the necessity of often costly and ineffective medications.

It is another object of the present invention to provide a therapeutic head supporting pillow which includes a pair of spaced pressure stimulators positioned to effectively contact an individual's accupressure points adjacent to their occipital nerves, thereby generating a therapeutic effect for relief of headaches and/or their onset.

Another object of the present invention is to provide a therapeutic pillow containing a freezable liquid which can be used to provide thermal relief to nerve areas for purposes of treating headaches and/or preventing their onset.

BRIEF DESCRIPTION OF THE DRAWINGS

The foregoing and other objects of the present invention will become apparent from the following description and the accompanying drawing figures, in which:

FIG. 1 is a top plan view of a therapeutic pillow in accordance with a preferred embodiment of the present invention;

FIG. 2 is a cross-sectional view of the therapeutic pillow of FIG. 1 taken along line 2—2;

FIG. 3 is a cross-sectional view of the therapeutic pillow of FIG. 1 taken along line 3—3;

FIG. 4 is a side illustrational view of an individual using the therapeutic pillow of FIG. 1 for supporting their head in accordance with a preferred embodiment of the present invention;

FIG. 5 is a bottom plan view of the individual using the therapeutic pillow of FIG. 4 in accordance with the present invention;

FIG. 6 is a plan view similar to FIG. 5 except without the therapeutic pillow for supporting the head and illustrating nerve pressure points; and FIG. 7 is top plan view of an embodiment of the therapeutic pillow which includes a strap for supporting the pillow against an individual in accordance with the present invention.

DESCRIPTION OF THE PREFERRED EMBODIMENTS

Referring to FIG. 1, the therapeutic pillow 10 of the present invention includes an outer cover 11 preferably composed of a soft nylon or other suitable and washable fabric material having opposite cover portions 11A and 11B. The cover may include an opening (not shown) closed by a fastener such as Velcro™ or a zipper. Inside of the cover 11 are housed a pair of pressure stimulators 12 and 13. The stimulators 12 and 13 are preferably substantially spherical and composed of rubber or other material and may have the approximate size (preferably not greater than about two and on-half inches in diameter) and consistency of tennis balls. A stabilizer bar 14 is fixed at each end to one of the stimulators 12 and 13 to maintain the stimulators in a fixed spaced relation.

A liquid which may be cooled or frozen is also housed within the cover 11. In the preferred embodiment, as shown in FIGS. 1–3, a pair of freezable packs or pouches 15 and 16 surround the stimulators 12 and 13. In some embodiments, a single pouch may be used. The presence of the packs 15 and 16 enables the pillow to be used to apply cold to the occipital nerves, or other areas, for purposes of providing pain abatement when in use. The pillow 10 may be stored in a freezer (not shown) so that the packs will be cooled or in a frozen or semi-frozen state when needed.

A resilient material layer 17, preferably a foam material, is also housed within the cover 11 to provide a cushioning function, and, in some uses, an insulating function.

The therapeutic pillow 10 is particularly adapted to be positioned beneath the area of an individual's neck. FIG. 6 shows an individual without the therapeutic pillow 10. The occipital nerve "N" and occipital arteries "A" are shown as well as pressure points P1 and P2 against which the present invention produces a therapeutic effect. FIG. 5 shows the same view with the therapeutic pillow in place and with the stimulators 12 and 13 producing a massaging pressure against the pressure points P1 and P2. Although not shown, the pillow may also be used for therapeutic and massage treatment of the lower back region by positioning the stimulators 12 and 13 on opposite sides of the spinal column.

When the pillow is in use, such as shown in FIG. 5, the freezable substance in the pouches or packs 15 and 16 will function to cool the nerve sites in the area of the individual's neck. The application of cold to these sites will have the effect of reducing the brain's response to headache pain by causing the nerves to flood the brain with conflicting or interfering signals brought about by the stimulation and sensation of cold produced against the skin.

One of the unique features of the present invention is that the pillow may be oriented such that either the pouches 15 and 16 containing the freezable substance is oriented upwardly so as to be close to the pressure point and nerves at the base of the individual's neck or adjacent the spinal column when applied along the small of the back in order to provide cold therapy treatment. However, the pillow can be reversed such that the foam material is positioned above the pouches 15 and 16 such that the cooling effect created by the freezable substance is minimized or reduced utilizing the foam layer 17 as an insulating barrier. In this manner, some of the cooling effect can be obtained by an indirect cooling of the nerves and pressure points when the pillow is in use.

A second embodiment of therapeutic pillow 10' is illustrated in FIG. 7 and includes a slot "S" at each end of the pillow. A strap 19 is extended through the slot "S" enabling the pillow 10' to be retained in place when an individual is in a standing, sitting or reclined position. The strap may be adjusted to produce a sufficient pressure against the individual's body.

The therapeutic pillows 10 or 10' are compactly shaped, being preferably approximately eight inches by ten inches.

The therapeutic pillow of the present invention can be used by an individual without any need for assistance. The pillow is preferably placed in a freezer so as to sufficiently chill the freezer packs 15 and 16. An individual with a headache, or feeling the onset of a headache, removes the pillow from the freezer and places the pillow on a firm, flat surface, such as a bed, the floor or the back of a chair. The individual then lies against a surface with the area along the neck resting on top of the pillow. The stimulators 12 and 13 produce a therapeutic effect against the pressure points at the back of the neck while the freezer packs 15 and 16 cool the neck area. The individual's head and neck provide ample weight to produce sufficient pressure against the pressure points.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims and their equivalents.

I claim:

1. A therapeutic pillow comprising:
    an outer cover having upper and lower surfaces;
    first and second pressure stimulators housed inside said outer cover and spaced from each other so as to be engageable through said upper and lower surfaces of said outer cover;
    a first layer of cushioning material housed inside said outer cover and adjacent said first and second pressure stimulators;
    a second layer of a freezable substance housed inside said outer cover adjacent said first and second pressure stimulators; and
    said first layer being positioned adjacent one of said upper and lower surfaces of said outer cover and said second layer being positioned adjacent the other of said upper and lower surfaces whereby said first layer, functions to thermally at least partially insulate said second layer from said other surface of said outer cover.

2. The therapeutic pillow of claim 1 further comprising a stabilizer bar mounted between said first and second pressure stimulators to maintain said first and second pressure stimulators in a fixed spacing relative to one another.

3. The therapeutic pillow of claim 2 wherein said first and second pressure stimulators are substantially spherical.

4. The therapeutic pillow of claim 3 wherein said first and second stimulators are each not greater than about two and one-half inches in diameter.

5. The therapeutic pillow of claim 1 further comprising:
    a strap; and
    means for securing said strap to said outer cover.

6. The therapeutic pillow of claim 1 wherein said first and second pressure stimulators are substantially spherical.

7. The therapeutic pillow of claim 6 wherein said first and second stimulators are each not greater than about two and one-half inches in diameter.

8. The therapeutic pillow of claim 1 wherein said freezable substance is enclosed inside at least one flexible pouch, said at least one pouch being housed inside said outer cover.

9. The therapeutic pillow of claim 8 including two flexible pouches.

10. The therapeutic pillow of claim 1 wherein said first and second stimulators are each not greater than about two and one-half inches in diameter.

11. The therapeutic pillow of claim 1 wherein said cushioning material is a foam material.

12. The therapeutic pillow of claim 1 wherein said outer cover is composed of a soft nylon material.

13. The therapeutic pillow of claim 1 wherein the outer cover includes opposite cover portions, said layer of cushioning material being mounted within said housing adjacent one of said opposite cover portions and said freezable substance being housed within said outer cover so as to create a layer adjacent the other of said opposite cover portions.

14. A therapeutic pillow comprising:
    an outer cover having opposing cover portions,
    first and second generally spherical pressure stimulators disposed within said outer cover and having oppositely oriented semispherical surface portions oriented toward said opposing cover portions,
    means for connecting said first and second pressure stimulators at a spaced distance from one another within said outer cover,
    at least one pouch containing a coolable liquid disposed within said outer cover so as to be adjacent one of said opposing cover portions thereof, and
    a layer of cushioning material disposed within said outer cover and positioned adjacent the other of said opposing cover portions whereby said therapeutic pillow may be utilized with either of the at least one pouch or the layer of cushioning material being oriented proximate of an individual utilizing the therapeutic pillow.

15. A therapeutic pillow comprising:
    an outer cover;
    first and second pressure stimulators housed inside said outer cover and spaced from each other;
    a stabilizer bar mounted between said first and second pressure stimulators to maintain said first and second pressure stimulators in a fixed spacing relative to one another;

a layer of cushioning material housed inside said outer cover; and a freezable substance housed inside said outer cover adjacent said first and second pressure stimulators.

16. The therapeutic pillow of claim 15 wherein said first and second pressure stimulators are substantially spherical.

17. The therapeutic pillow of claim 16 wherein said first and second stimulators are each not greater than about two and one-half inches in diameter.

* * * * *